(12) United States Patent
Gross (10) Patent No.: US 9,386,991 B2
(45) Date of Patent: Jul. 12, 2016

(54) PRESSURE-ENHANCED BLOOD FLOW TREATMENT

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzeliya (IL)

( * ) Notice: Subject to any disclaimer, the term of this patent is extended or adjusted under 35 U.S.C. 154(b) by 582 days.

(21) Appl. No.: 13/755,662

(22) Filed: Jan. 31, 2013

(65) Prior Publication Data

US 2013/0204292 A1 Aug. 8, 2013

Related U.S. Application Data

(60) Provisional application No. 61/593,915, filed on Feb. 2, 2012.

(51) Int. Cl.
| | |
|---|---|
| *A61B 17/00* | (2006.01) |
| *A61B 17/12* | (2006.01) |
| *A61F 2/06* | (2013.01) |
| *A61F 2/24* | (2006.01) |
| *A61N 1/36* | (2006.01) |
| *A61B 5/00* | (2006.01) |
| *A61B 5/02* | (2006.01) |

(Continued)

(52) U.S. Cl.
CPC . *A61B 17/12* (2013.01); *A61F 2/06* (2013.01); *A61F 2/24* (2013.01); *A61N 1/36007* (2013.01); *A61B 5/02* (2013.01); *A61B 5/6876* (2013.01); *A61B 2017/00022* (2013.01); *A61B 2017/00132* (2013.01); *A61F 2/2475* (2013.01); *A61N 1/3627* (2013.01); *A61N 1/36564* (2013.01)

(58) Field of Classification Search
CPC .......... A61F 2/24; A61F 2/06; A61F 2/2475; A61N 1/362; A61N 1/36564; A61N 1/3627; A61B 5/02; A61B 5/6876; A61B 2017/00022
See application file for complete search history.

(56) References Cited

U.S. PATENT DOCUMENTS

| 3,650,277 A | 3/1972 | Sjostrand et al. |
| 3,661,148 A | 5/1972 | Kolin |

(Continued)

FOREIGN PATENT DOCUMENTS

| CN | 1878595 | 11/2010 |
| EP | 0 109 935 | 5/1984 |

(Continued)

OTHER PUBLICATIONS

Sherman AJ, "Blockade of nitric oxide synthesis reduces myocardial oxygen consumption in vivo", Circulation 95:1328-1334, 1997.

(Continued)

*Primary Examiner* — Ashley Fishback
(74) *Attorney, Agent, or Firm* — Sughrue Mion, PLLC (57) ABSTRACT

Apparatus and methods are provided, including a sensor, configured to sense a cardiac cycle of a patient and to generate a signal in response thereto. A pressure mechanism is coupled to a site of an artery of the patient, and, in response to the signal, enhances blood flow of the patient in a downstream direction by compressing the artery. A valve is implanted upstream of the site, and inhibits blood flow in an upstream direction due to operation of the pressure mechanism. Other applications are also described.

6 Claims, 4 Drawing Sheets

(51) Int. Cl.
    *A61N 1/362*        (2006.01)
    *A61N 1/365*        (2006.01)

(56) References Cited

U.S. PATENT DOCUMENTS

| | | | |
|---|---|---|---|
| 4,154,227 A | 5/1979 | Krause et al. |
| 4,201,219 A | 5/1980 | Bozal |
| 4,474,630 A | 10/1984 | Planck et al. |
| 4,546,759 A | 10/1985 | Solar |
| 4,753,221 A | 6/1988 | Kensey et al. |
| 4,791,931 A | 12/1988 | Slate |
| 4,821,723 A | 4/1989 | Baker et al. |
| 4,938,766 A | 7/1990 | Jarvik |
| 4,943,277 A | 7/1990 | Bolling |
| 5,192,271 A | 3/1993 | Kalb et al. |
| 5,265,011 A | 11/1993 | O'Rourke et al. |
| 5,265,601 A | 11/1993 | Mehra |
| 5,304,208 A | 4/1994 | Inguaggiato et al. |
| 5,324,323 A | 6/1994 | Bui |
| 5,330,507 A | 7/1994 | Schwartz |
| 5,372,573 A | 12/1994 | Habib |
| 5,411,031 A | 5/1995 | Yomtov |
| 5,423,871 A | 6/1995 | Hoegnelid et al. |
| 5,454,838 A | 10/1995 | Vallana et al. |
| 5,458,626 A | 10/1995 | Krause |
| 5,487,760 A | 1/1996 | Villafana |
| 5,509,428 A | 4/1996 | Dunlop |
| 5,540,733 A | 7/1996 | Testerman et al. |
| 5,549,655 A | 8/1996 | Erickson |
| 5,591,216 A | 1/1997 | Testerman et al. |
| 5,612,314 A | 3/1997 | Stamler |
| 5,645,839 A | 7/1997 | Chobanian et al. |
| 5,649,966 A | 7/1997 | Noren et al. |
| 5,669,924 A | 9/1997 | Shaknovich |
| 5,707,400 A | 1/1998 | Terry, Jr. et al. |
| 5,762,599 A | 6/1998 | Sohn |
| 5,782,774 A | 7/1998 | Shmulewitz |
| 5,800,375 A | 9/1998 | Sweezer et al. |
| 5,800,464 A | 9/1998 | Kieval et al. |
| 5,800,502 A | 9/1998 | Boutos |
| 5,810,757 A | 9/1998 | Sweezer et al. |
| 5,900,433 A | 5/1999 | Igo et al. |
| 5,904,712 A | 5/1999 | Axelgaard |
| 5,906,641 A | 5/1999 | Thompson |
| 5,913,876 A | 6/1999 | Taylor |
| 5,925,061 A | 7/1999 | Ogi et al. |
| 5,935,077 A | 8/1999 | Ogle |
| 5,944,680 A | 8/1999 | Christopherson |
| 5,967,986 A | 10/1999 | Cimochowski et al. |
| 5,994,444 A | 11/1999 | Trescony et al. |
| 6,023,640 A | 2/2000 | Ross |
| 6,038,485 A | 3/2000 | Axelgaard |
| 6,053,873 A | 4/2000 | Govari |
| 6,058,331 A | 5/2000 | King |
| 6,086,527 A | 7/2000 | Talpade |
| 6,106,477 A | 8/2000 | Miesel et al. |
| 6,120,520 A | 9/2000 | Saadat |
| 6,139,487 A | 10/2000 | Siess |
| 6,141,587 A | 10/2000 | Mower et al. |
| 6,200,259 B1 | 3/2001 | March |
| 6,212,435 B1 | 4/2001 | Lattner et al. |
| 6,240,316 B1 | 5/2001 | Richmond et al. |
| 6,245,103 B1 | 6/2001 | Stinson |
| 6,277,078 B1 | 8/2001 | Porat et al. |
| 6,280,377 B1 | 8/2001 | Talpade |
| 6,345,202 B2 | 2/2002 | Richmond et al. |
| 6,347,247 B1 | 2/2002 | Dev |
| 6,411,845 B1 | 6/2002 | Mower et al. |
| 6,445,953 B1 | 9/2002 | Bulkes |
| 6,459,928 B2 | 10/2002 | Mika et al. |
| 6,463,323 B1 | 10/2002 | Conrad-Vlasak |
| 6,485,524 B2 | 11/2002 | Strecker |
| 6,508,777 B1 | 1/2003 | Macoviak et al. |
| 6,522,926 B1 | 2/2003 | Kieval et al. |
| 6,575,994 B1 | 6/2003 | Marin et al. |
| 6,602,270 B2 | 8/2003 | Leschinsky et al. |
| 6,616,613 B1 | 9/2003 | Goodman et al. |
| 6,616,624 B1 | 9/2003 | Kieval et al. |
| 6,618,627 B2 | 9/2003 | Lattner et al. |
| 6,622,041 B2 | 9/2003 | Terry, Jr. et al. |
| 6,632,991 B2 | 10/2003 | Chen |
| 6,641,542 B2 | 11/2003 | Cho et al. |
| 6,647,287 B1 | 11/2003 | Peel, III |
| 6,721,603 B2 | 4/2004 | Zabara et al. |
| 6,733,459 B1 | 5/2004 | Atsumi |
| 6,770,022 B2 | 8/2004 | Mechlenburg |
| 6,810,286 B2 | 10/2004 | Donovan |
| 6,824,561 B2 | 11/2004 | Soykan |
| 6,845,267 B2 | 1/2005 | Harrison |
| 6,850,801 B2 | 2/2005 | Kieval et al. |
| 6,865,416 B2 | 3/2005 | Dev et al. |
| 6,871,092 B2 | 3/2005 | Piccone |
| 6,885,895 B1 | 4/2005 | Whitehurst |
| 6,939,345 B2 | 9/2005 | KenKnight |
| 6,947,792 B2 | 9/2005 | Ben-Haim et al. |
| 6,985,774 B2 | 1/2006 | Kieval et al. |
| 7,025,730 B2 | 4/2006 | Cho et al. |
| 7,044,981 B2 | 5/2006 | Liu et al. |
| 7,056,336 B2 | 6/2006 | Armstrong et al. |
| 7,062,318 B2 | 6/2006 | Ben-Haim et al. |
| 7,082,336 B2 | 7/2006 | Ransbury et al. |
| 7,090,648 B2 | 8/2006 | Sackner et al. |
| 7,158,832 B2 | 1/2007 | Kieval et al. |
| 7,159,593 B2 | 1/2007 | McCarthy et al. |
| 7,167,748 B2 | 1/2007 | Ben-Haim et al. |
| 7,167,751 B1 | 1/2007 | Whitehurst et al. |
| 7,206,637 B2 | 4/2007 | Salo |
| 7,225,019 B2 | 5/2007 | Jahns et al. |
| 7,229,403 B2 | 6/2007 | Schock |
| 7,269,457 B2 | 9/2007 | Shafer et al. |
| 7,277,749 B2 | 10/2007 | Gordon et al. |
| 7,291,113 B2 | 11/2007 | Satoh |
| 7,292,886 B1 | 11/2007 | Kroll |
| 7,299,091 B2 | 11/2007 | Barrett et al. |
| 7,389,149 B2 | 6/2008 | Rossing et al. |
| 7,395,119 B2 | 7/2008 | Hagen et al. |
| 7,452,334 B2 | 11/2008 | Gianchandani |
| 7,476,200 B2 | 1/2009 | Tal |
| 7,483,743 B2 | 1/2009 | Mann et al. |
| 7,486,991 B2 | 2/2009 | Libbus et al. |
| 7,614,998 B2 | 11/2009 | Gross |
| 7,623,926 B2 | 11/2009 | Rossing et al. |
| 7,660,632 B2 | 2/2010 | Kirby et al. |
| 7,680,538 B2 | 3/2010 | Durand et al. |
| 7,706,884 B2 | 4/2010 | Libbus |
| 7,706,886 B2 | 4/2010 | Morimoto et al. |
| 7,734,348 B2 | 6/2010 | Zhang et al. |
| 7,747,302 B2 | 6/2010 | Milledge |
| 7,765,000 B2 | 7/2010 | Zhang et al. |
| 7,797,050 B2 | 9/2010 | Libbus et al. |
| 7,811,221 B2 | 10/2010 | Gross |
| 7,853,305 B2 | 12/2010 | Simon et al. |
| 8,070,708 B2 | 12/2011 | Rottenberg et al. |
| 8,249,705 B1 | 8/2012 | Kieval |
| 8,252,018 B2 | 8/2012 | Valaie |
| 8,538,535 B2 | 9/2013 | Gross et al. |
| 2001/0044434 A1 | 11/2001 | Lee et al. |
| 2002/0016615 A1 | 2/2002 | Dev |
| 2002/0026228 A1 | 2/2002 | Schauerte |
| 2002/0032468 A1 | 3/2002 | Hill |
| 2002/0077554 A1 | 6/2002 | Schwartz |
| 2002/0103454 A1 | 8/2002 | Sackner |
| 2002/0103501 A1 | 8/2002 | Diaz et al. |
| 2002/0169413 A1 | 11/2002 | Keren |
| 2003/0036773 A1 | 2/2003 | Whitehurst |
| 2003/0050683 A1 | 3/2003 | Boutos |
| 2003/0060858 A1 | 3/2003 | Kieval et al. |
| 2003/0130715 A1 | 7/2003 | Boutos |
| 2003/0199806 A1 | 10/2003 | Kieval |
| 2003/0204206 A1 | 10/2003 | Padua |
| 2004/0010303 A1 | 1/2004 | Bolea et al. |
| 2004/0019364 A1 | 1/2004 | Kieval et al. |
| 2004/0019368 A1 | 1/2004 | Lattner et al. |
| 2004/0039417 A1 | 2/2004 | Soykan |

(56) References Cited

U.S. PATENT DOCUMENTS

| | | |
|---|---|---|
| 2004/0044393 A1 | 3/2004 | Yarden |
| 2004/0054384 A1 | 3/2004 | Nachum |
| 2004/0064090 A1 | 4/2004 | Keren |
| 2004/0106954 A1 | 6/2004 | Whitehurst et al. |
| 2004/0106976 A1 | 6/2004 | Bailey et al. |
| 2004/0111006 A1 | 6/2004 | Adams |
| 2004/0133240 A1 | 7/2004 | Adams |
| 2004/0162514 A1 | 8/2004 | Alferness et al. |
| 2004/0162590 A1 | 8/2004 | Whitehurst et al. |
| 2004/0193092 A1 | 9/2004 | Deal |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0049680 A1 | 3/2005 | Fischell et al. |
| 2005/0090867 A1 | 4/2005 | Lapanashvili |
| 2005/0096710 A1 | 5/2005 | Kieval et al. |
| 2005/0143785 A1 | 6/2005 | Libbus |
| 2005/0148925 A1 | 7/2005 | Rottenberg et al. |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0154418 A1 | 7/2005 | Kieval et al. |
| 2005/0165457 A1 | 7/2005 | Benser et al. |
| 2005/0203610 A1 | 9/2005 | Tzeng |
| 2005/0209652 A1 | 9/2005 | Whitehurst et al. |
| 2005/0232965 A1 | 10/2005 | Falotico |
| 2005/0233962 A1 | 10/2005 | Lue et al. |
| 2005/0240229 A1 | 10/2005 | Whitehurst et al. |
| 2005/0245893 A1 | 11/2005 | Leschinsky |
| 2005/0251212 A1 | 11/2005 | Kieval et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0064059 A1 | 3/2006 | Gelfand et al. |
| 2006/0074453 A1 | 4/2006 | Kieval et al. |
| 2006/0100668 A1 | 5/2006 | Ben-David |
| 2006/0111626 A1 | 5/2006 | Rossing et al. |
| 2006/0149124 A1 | 7/2006 | Forsell |
| 2006/0149345 A1 | 7/2006 | Boggs et al. |
| 2006/0167539 A1 | 7/2006 | McEwan |
| 2006/0167540 A1 | 7/2006 | Masters et al. |
| 2006/0173507 A1 | 8/2006 | Mrva et al. |
| 2006/0206029 A1 | 9/2006 | Yair |
| 2006/0217588 A1 | 9/2006 | Gross et al. |
| 2006/0217772 A1 | 9/2006 | Libbus et al. |
| 2006/0229677 A1 | 10/2006 | Moffit et al. |
| 2006/0259085 A1 | 11/2006 | Zhang et al. |
| 2006/0265038 A1 | 11/2006 | Hagen et al. |
| 2006/0276844 A1 | 12/2006 | Alon |
| 2006/0293712 A1 | 12/2006 | Kieval et al. |
| 2007/0005010 A1 | 1/2007 | Mori et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0083258 A1 | 4/2007 | Falotico |
| 2007/0100430 A1 | 5/2007 | Rudakov et al. |
| 2007/0100433 A1 | 5/2007 | Limon |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156167 A1 | 7/2007 | Connors |
| 2007/0156179 A1 | 7/2007 | S.E. |
| 2007/0156198 A1 | 7/2007 | Rossing et al. |
| 2007/0156201 A1 | 7/2007 | Rossing et al. |
| 2007/0167984 A1 | 7/2007 | Kieval et al. |
| 2007/0173893 A1 | 7/2007 | Pitts |
| 2007/0185542 A1 | 8/2007 | Bolea et al. |
| 2007/0185543 A1 | 8/2007 | Rossing et al. |
| 2007/0191904 A1 | 8/2007 | Libbus et al. |
| 2007/0196428 A1 | 8/2007 | Glauser et al. |
| 2007/0198064 A1 | 8/2007 | Lapanashvili et al. |
| 2007/0248676 A1 | 10/2007 | Stamler et al. |
| 2007/0248850 A1 | 10/2007 | Heller |
| 2007/0274565 A1 | 11/2007 | Penner |
| 2007/0276270 A1 | 11/2007 | Tran |
| 2007/0276442 A1 | 11/2007 | Hagen et al. |
| 2007/0276459 A1 | 11/2007 | Rossing et al. |
| 2007/0282385 A1 | 12/2007 | Rossing et al. |
| 2007/0293927 A1 | 12/2007 | Frank et al. |
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0046016 A1 | 2/2008 | Ben-David |
| 2008/0046054 A1 | 2/2008 | Hjelle et al. |
| 2008/0051767 A1 | 2/2008 | Rossing et al. |
| 2008/0058872 A1 | 3/2008 | Brockway et al. |
| 2008/0071363 A1 | 3/2008 | Tuval et al. |
| 2008/0082137 A1 | 4/2008 | Kieval et al. |
| 2008/0097540 A1 | 4/2008 | Bolea et al. |
| 2008/0119898 A1 | 5/2008 | Ben-David |
| 2008/0119911 A1 | 5/2008 | Rosero |
| 2008/0132972 A1 | 6/2008 | Shuros et al. |
| 2008/0140167 A1 | 6/2008 | Hagen et al. |
| 2008/0154349 A1 | 6/2008 | Rossing et al. |
| 2008/0161865 A1 | 7/2008 | Hagen et al. |
| 2008/0161887 A1 | 7/2008 | Hagen et al. |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177364 A1 | 7/2008 | Bolea et al. |
| 2008/0195174 A1 | 8/2008 | Walker et al. |
| 2008/0215117 A1 | 9/2008 | Gross |
| 2008/0269871 A1 | 10/2008 | Eli |
| 2009/0005859 A1 | 1/2009 | Keilman |
| 2009/0030471 A1 | 1/2009 | Rousso et al. |
| 2009/0036975 A1 | 2/2009 | Ward |
| 2009/0062874 A1 | 3/2009 | Tracey et al. |
| 2009/0112285 A1 | 4/2009 | Cahan et al. |
| 2009/0118785 A1 | 5/2009 | Ignagni et al. |
| 2009/0137968 A1 | 5/2009 | Rottenberg |
| 2009/0177090 A1 | 7/2009 | Grunwald et al. |
| 2009/0198097 A1 | 8/2009 | Gross |
| 2009/0198308 A1 | 8/2009 | Gross |
| 2009/0204170 A1 | 8/2009 | Hastings |
| 2009/0228078 A1 | 9/2009 | Zhang et al. |
| 2010/0010556 A1 | 1/2010 | Zhao |
| 2010/0042186 A1 | 2/2010 | Ben-David et al. |
| 2010/0076247 A1 | 3/2010 | Zilbershlag |
| 2010/0094373 A1 | 4/2010 | Sharma |
| 2010/0125310 A1 | 5/2010 | Wilson et al. |
| 2010/0185255 A1 | 7/2010 | Libbus |
| 2010/0211131 A1 | 8/2010 | Williams et al. |
| 2010/0222832 A1 | 9/2010 | Zhang et al. |
| 2010/0305392 A1 | 12/2010 | Gross et al. |
| 2011/0118773 A1 | 5/2011 | Gross |
| 2012/0035645 A1 | 2/2012 | Gross |
| 2012/0035711 A1 | 2/2012 | Gross et al. |
| 2012/0123498 A1 | 5/2012 | Gross |
| 2013/0123569 A1 | 5/2013 | Gross |

FOREIGN PATENT DOCUMENTS

| | | |
|---|---|---|
| EP | 0791341 | 8/1997 |
| WO | 99/26530 | 6/1999 |

(56) References Cited

FOREIGN PATENT DOCUMENTS

| WO | 00/02501 | 1/2000 |
|---|---|---|
| WO | 02/26314 | 4/2002 |
| WO | 03/076008 | 9/2003 |
| WO | 03/082080 | 10/2003 |
| WO | 03/082403 | 10/2003 |
| WO | 2004/064729 | 8/2004 |
| WO | 2004/073484 | 9/2004 |
| WO | 2004/073796 | 9/2004 |
| WO | 2005/042083 | 5/2005 |
| WO | 2005/065771 | 7/2005 |
| WO | 2005/084389 | 9/2005 |
| WO | 2005/097256 | 10/2005 |
| WO | 2006/012033 | 2/2006 |
| WO | 2006/012050 | 2/2006 |
| WO | 2006/032902 | 3/2006 |
| WO | 2006/041664 | 4/2006 |
| WO | 2006/064503 | 6/2006 |
| WO | 2006/094273 | 9/2006 |
| WO | 2006/098928 | 9/2006 |
| WO | 2006/120464 | 11/2006 |
| WO | 2006/123346 | 11/2006 |
| WO | 2006/125163 | 11/2006 |
| WO | 2007/013065 | 2/2007 |
| WO | 2007/047152 | 4/2007 |
| WO | 2007/064895 | 6/2007 |
| WO | 2007/083288 | 7/2007 |
| WO | 2007/106533 | 9/2007 |
| WO | 2007/113818 | 10/2007 |
| WO | 2007/113833 | 10/2007 |
| WO | 2007/114860 | 10/2007 |
| WO | 2007/118090 | 10/2007 |
| WO | 2007/136850 | 11/2007 |
| WO | 2007/136851 | 11/2007 |
| WO | 2008/003501 | 1/2008 |
| WO | 2008/039982 | 4/2008 |
| WO | 2008/083120 | 7/2008 |
| WO | 2008/083235 | 7/2008 |
| WO | 2008/100390 | 9/2008 |
| WO | 2009/017647 | 2/2009 |
| WO | 2009/095918 | 8/2009 |
| WO | 2009/095920 | 8/2009 |
| WO | 2012/066532 | 5/2012 |

OTHER PUBLICATIONS

U.S. Appl. No. 61/593,915, filed Feb. 2, 2012.
Kugiyama K, "Nitric oxide activity is deficient in spasm arteries of patients with coronary spastic angina", Circulation 94:266-272, 1996.
Sabbah H et al., "Global left ventricular remodeling with the Acorn Cardiac Support Device: Hemodynamic and angiographic findings in dogs with heart failure", Heart Failure 10(2): 109-115, 2005. (Only First Page).
Schoenfisch et al., "Improving the Thromboresistivity of Chemical Sensors via Nitric Oxide Release: Fabrication and in Vivo Evaluation of NO-Releasing Oxygen-Sensing Catheters," Anal. Chem., 72 (6), 1119-1126, 2000.
Yao et al., "Endogenous and Exogenous Nitric Oxide Protect Against Intracoronary Thrombosis and Reocclusion After Thrombolysis," Circulation. 1995;92: 1005-1010.
Shin et al., "Improving the biocompatibility of in vivo sensors via nitric oxide release," Analyst, 2006, 131, 609-615.
Cheetah Medical Inc. manufactures the Cheetah Reliant, Jan. 23, 2008.
CardioMEMS, Inc., manufactures the EndoSure® Wireless AAA Pressure Measurement System, Nov. 11, 2005.
Sulzer IntraTherapeutics Inc. manufactures the IntraCoil® Self-Expanding Peripheral Stent (IntraCoil® Stent), Jun. 28, 2002.
Hayashida, et al., "Comparison of neurogenic contraction and relaxation in canine corpus cavernosum and penile artery and vein", Jpn. J. Pharmacol. 72:231-240 (1996), p. 232 col. 2, para 1; p. 238, col. 2. para 2.

An International Search Report and a Written Opinion both dated Jul. 13, 2009, which issued during the prosecution of Applicant's PCT/IL09/00117.
An International Search Report dated May 12, 2009, which issued during the prosecution of Applicant's PCT/IL09/00115.
A Restriction Requirement dated Jun. 7, 2012, which issued during the prosecution of U.S. Appl. No. 12/851,214.
An Office Action dated Nov. 18, 2009, which issued during the prosecution of Applicant's U.S. Appl. No. 12/023,900.
An Office Action dated Oct. 2, 2012, which issued during the prosecution of U.S. Appl. No. 12/851,214.
Matheny, "Vagus nerve stimulation as a method to temporarily slow or arrest the heart," Ann Thorac Surg. Jun. 1997:63(6 Suppl):S28-9—an abstract.
A Notice of Alowance dated May 17, 2013, which issued during the prosecution of U.S. Appl. No. 12/851,214.
Task Force of the European Society of Cardiology and the North American Society of Pacing and Electrophysiology, "Heart rate variability," European Heart Journal (1996) 17, 354-381.
Vallais, "Heart rate and vasomotor control during exercise,", Proceedings of the 29th Annual International Conference of the IEEE EMBS, Cite Internationale, Lyon, France, Aug. 23-26, 2007.
Wustmann, "Effects of chronic baroreceptor stimulation on the autonomic cardiovascular regulation in patients with drug-resistant arterial hypertension," Hypertension 2009;54;530-536.
Biosense Webster, Inc. (CA, USA) manufactures the LASSO 2515 Variable Circular Mapping Catheter.
Laitinen, "Sympathovagal balance is major determinant of short-term blood pressure variability in healthy subjects,"Am J Physiol Heart Circ Physiol 276:1245-1252, 1999.
Baudrie, "Optimal frequency ranges for extracting information on cardiovascular autonomic control from the blood pressure and pulse interval spectrograms in mice," Am J Physiol Regul Integr Comp Physiol 292: R904-R912, 2007.
Malpas, "Neural influences on cardiovascular variability: possibilities and pitfalls," Am J Physiol Heart Circ Physiol 282: H6-H20, 2002.
Lewis, "Vagus nerve stimulation decreases left ventricular contractility in vivo in the human and pig heart," J Physiol. Jul. 15, 2001; 534(Pt 2): 547-552.
An International Preliminary Examination Report on Patentability dated Aug. 3, 2010, which issued during the prosecution of Applicant's PCT/IL09/00117.
A Restriction Requirement dated Sep. 20, 2012, which issued during the prosecution of U.S. Appl. No. 12/851,263.
An International Preliminary Examination Report on Patentability dated Aug. 3, 2010, which issued during the prosecution of Applicant's PCT/IL09/00115.
An Office Action dated Dec. 6, 2012, which issued during the prosecution of U.S. Appl. No. 12/851,263.
Frost, et al., "Preparation and characterization of implantable sensors with nitric oxide release coating", Microchemical Journal vol. 74 Issue: Jun. 3, 2003, pp. 277-288.
Paulus WJ, "Beneficial effects of nitric oxide on cardiac diastolic function: the flip side of the coin", Heart Failure Review 5(4): 337-344 (2000).
Zhao et al., "Loss of nitric oxide production in the coronary circulation after the development of dilated cardiomyopathy: a specific defect in the neural regulation of coronary blood flow", Clinical and Experimental Pharmacology and Physiology 23(8): 715-721 (1996).
A Supplementary European search Report dated Dec. 14, 2012, which issued during the prosecution of European Patent Application No. 06766171.
An Office Action dated Sep. 18, 2012, which issued during the prosecution of U.S. Appl. No. 12/023,896.
An English Translation of an Office Action dated Oct. 8, 2012, which issued during the prosecution of Chinese Patent Application No. 200980111617.8.
An Office Action dated Jun. 19, 2012, which issued during the prosecution of U.S. Appl. No. 11/995,904.
An Office Action dated Jul. 18, 2012, which issued during the prosecution of U.S. Appl. No. 13/210,778.

(56) References Cited

OTHER PUBLICATIONS

An International Search Report and a Written Opinion both dated Dec. 19, 2011, which issued during the prosecution of Applicant's PCT/IL11/00636.

An Office Action dated Mar. 13, 2012, which issued during the prosecution of U.S. Appl. No. 12/023,896.

An Office Action dated Aug. 29, 2012, which issued during the prosecution of U.S. Appl. No. 12/792,227.

An Office Action dated Aug. 1, 2012, which issued during the prosecution of U.S. Appl. No. 12/957,799.

An Office Action dated Mar. 15, 2012, which issued during the prosecution of U.S. Appl. No. 12/792,227.

An International Search Report and a Written Opinion both dated Jul. 5, 2012, which issued during the prosecution of Applicant's PCT/IL11/00952.

Taylor, The unequal influences of the left and right vagi on the control of the heart and pulmonary artery in the rattlesnake. Crotalus durissus, The Journal of Experimental Biology 212, 145-151 Aug. 2008.

Hamiton,"Coronary vascular sympathetic beta-receptor innervation," American Journal of Physiology, vol. 230, No. 6, Jun. 1976.

An Office Action dated Aug. 9, 2011, which issued during the prosecution of U.S. Appl. No. 12/023,896.

An International Search Report and a Written Opinion both dated Aug. 8, 2013, which issued during the prosecution of Applicant's PCT/IL2013/050375.

Office Action issued in U.S. Appl. No. 13/294,062, dated Dec. 13, 2013.

C. de Balthasar et al. "Attachment of leads to RF-BION microstimulators."

D.W. Eisele, "Tongue neuromuscular and direct hypoglossal nerve stimulation for obstructive sleep apnea." Otolaryngologic clinics of North America, vol. 36, 2003, p. 501.

G.E. Loeb et al. "RF-powered BIONs for stimulation and sensing." Engineering in Medicine and Biology Society, 2004, IEMBS'04, 26th Annual International Conference of the IEEE, 2005, pp. 4182-4185.

G.E. Loeb et al. "The BION devices: injectable interfaces with peripheral nerves and muscles," Neurosurgical Focus, vol. 20, 2006, pp. 1-9.

E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.

A. Oliven et al. "Sublingual electrical stimulation of the tongue during wakefulness and sleep," Respiration physiology, vol. 127, 2001, pp. 217-226.

A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.

A. Oliven, M. Odeh, L. Geitini, R. Oliven, U. Steinfeld, A.R. Schwartz, and N. Toy, "Effect of coactivation of tongue protrusor and retractor muscles on pharyngeal lumen and airflow in sleep apnea patients," Journal of Applied Physiology, vol. 103, 2007, p. 1662.

A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.

W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.

W.H. Tran, G.E. Loeb, F.J.R. Richmond, R. Ahmed, G.T. Clark, and P.B. Haberman, "First subject evaluated with simulated BIONTM treatment in genioglossus to prevent obstructive sleep apnea," Engineering in Medicine and Biology Society, 2004. IEMBS'04. 26th Annual International Conference of the IEEE, 2005, pp. 4287-4289.

P• R• Troyk, "Injectable electronic identification, monitoring, and stimulation systems," Biomedical Engineering, vol. 1, 1999, p. 177.

T.K. Whitehurst, J.H. Schulman, K.N. Jaax, and R. Carbunaru, "The Bion® Microstimulator and its Clinical Applications," Implantable Neural Prostheses 1, 2009, pp. 253-273.

D• J• Young, "Wireless powering and data telemetry for biomedical implants," Engineering in Medicine and Biology Society, 2009. EMBC 2009. Annual International Conference of the IEEE, 2009, pp. 3221-3224.

Reid R. Harrison, et al., "Wireless Neural Recording with Single Low-Power Integrated Circuit", IEEE Trans Neural Syst Rehabil Eng. Aug. 2009; 17(4): 322-329.

An International Search Report which issued during the prosecution and a Written Opinion both dated Apr. 17, 2012 of Applicant's PCT/IL11/00870.

Patents Galore: Implantable Neurostimulators Fight Snoring and Corpse Eye-Proof Scanners. Printout from http://medgadget.com/2006/03patents_galore.html (Downloaded Jan. 2012).

A heart pump without a cord, MIT Technology Review, Jul. 18, 2011 http://www.technologyreview.com/biornedicine/38064/.

An Office Action dated May 11, 2012, which issued during the prosecution of U.S. Appl. No. 12/946,246.

U.S. Appl. No. 60/541,267 to Rottenberg filed Feb. 3, 2004.

U.S. Appl. No. 60/573,378 to Rottenberg filed May 24, 2004.

U.S. Appl. No. 60/761,192 to Rozy filed Jan. 23, 2006.

U.S. Appl. No. 60/862,496 to Levi filed Oct. 23, 2006.

PRESSURE-ENHANCED BLOOD FLOW TREATMENT

CROSS-REFERENCES TO RELATED APPLICATIONS

The present application claims the benefit of U.S. Provisional Patent Application 61/593,915 to Gross, filed Feb. 2, 2012, entitled "Pressure-enhanced blood flow treatment," which is incorporated herein by reference.

FIELD OF THE INVENTION

The present invention relates generally to a medical device, and specifically to methods and apparatus that enhance blood flow in a blood vessel.

BACKGROUND

The narrowing or blockage of arteries, which results in obstructions to blood flow, may cause an insufficient supply of oxygen to body tissues, which may ultimately lead to loss of function of these tissues. These obstructions may occur when a blood clot or a fatty deposit arrive from a first artery through the bloodstream (e.g., from the aorta) and settle in a portion of a second artery, thereby causing narrowing or blockage of the second artery. Alternatively, an obstruction may be generated from the formation of a blood clot in the artery itself, usually where the artery has been damaged due to a disease of the artery. Causes for such damage may be a medical procedure, atherosclerosis, inflammation of the artery, or an aneurysm.

In addition, blood flow in an artery may be low due to a patient having a weak heart, e.g., due to the patient suffering from heart failure, due to nerve damage, or due to other factors.

SUMMARY OF APPLICATIONS

For some applications of the present invention, a system for enhancing blood flow in a blood vessel of a patient comprises a sensor, a pressure mechanism and a valve. Typically, but not necessarily, the valve is obtained from a source of commercially-available aortic valves. For some applications of the present invention, the valve is implanted at least five centimeters downstream of the native aortic valve site, for example between the renal artery and the bifurcation of the aorta with the iliac arteries.

According to one application of the present invention, the blood vessel of the patient is an artificial blood vessel (i.e., a graft), configured to be inserted into a peripheral arterial site, which, in the context of the present application, comprises any arterial site downstream of the implanted valve.

For some applications, a portion (e.g., a 10-40 cm portion) of the femoral artery may be excised and replaced with a blood vessel graft in at least one leg of the patient. (For example, a graft may be placed in each leg.) Alternatively, the blood vessel is a natural vessel of the patient.

For some applications of the present invention, the sensor is configured to sense a cardiac cycle of the patient and to generate a signal in response to that signal. For some applications of the present invention, the pressure mechanism is coupled to a site on the blood vessel of the patient, and is configured to respond to the generated signal by compressing the blood vessel during diastole and releasing the compression during systole, thereby enhancing blood flow of the patient in the downstream direction.

The valve is typically implanted upstream of the arterial site to which the pressure mechanism is coupled, thereby inhibiting blood flow in an upstream direction due to the operation of the pressure mechanism. Typically, the valve is not physically coupled to the pressure mechanism, i.e., the valve is not part of one integrated assembly with the pressure mechanism. Alternatively, the valve and the pressure mechanism comprise one integrated assembly. In one application of the present invention, the valve is configured to be implanted in the artery upstream to the arterial site to which the pressure mechanism is coupled. In another application of the present invention, the valve is configured to be implanted in an artery other than the arterial site to which the pressure mechanism is coupled, e.g., in the aorta of the patient.

For some applications of the present invention, the pressure mechanism comprises one or more electrodes, configured to be placed in contact with the artery. These electrodes are coupled to a control unit, which is configured to drive the electrodes to drive a contraction-inducing current into the site of the artery during diastole, and to withhold driving the electrodes to drive such a current during systole. Alternatively, the pressure mechanism comprises a mechanical compressor, a cuff, a pump or a solenoid. Other pressure mechanisms may also be used (e.g., extracorporeal pressure mechanisms, such as an external cuff, or pressure-application pants which are typically configured for applying external counterpulsation).

For some applications of the present invention, the graft is implanted downstream of the valve. For some applications of the present invention, the graft is compliant, and changes its cross-sectional area according to the cardiac cycle of the patient. For example, the graft expands during systole, and contracts during diastole. Typically, the diastolic contraction of the graft squeezes out blood that is in the contracting area of the graft. According to one application of the present invention, the implanted valve inhibits the upstream flow of blood from the contracting graft, therefore enhancing the blood flow in a downstream direction due to the contraction of the graft. Although typically the valve is implanted in the aorta, for some applications, the valve may be implanted in an artery which is smaller in diameter than the aorta.

According to one application of the present invention, the graft expands during systole without any change in the shape of the graft (e.g., both the pre-expansion and post-expansion shapes of the graft may be circular). Alternatively, the graft changes its cross-sectional shape from an ellipse in diastole to a circle in systole. The cross-sectional area thus goes up substantially during systole.

For some applications of the present invention, the valve is physically coupled to the graft. Alternatively, the valve is implanted in a different artery than the graft.

It is noted that the scope of the present invention includes implanting the valve before the pressure mechanism, as well as implanting the valve after the pressure mechanism.

There is therefore provided, in accordance with an application of the present invention, apparatus, including:

a sensor, configured to sense a cardiac cycle of a patient and to generate a signal in response thereto;

a pressure mechanism, configured to be coupled to a site of an artery of the patient, and, in response to the signal, to enhance blood flow of the patient in a downstream direction by compressing the artery; and a valve, configured to be implanted upstream of the site, and to inhibit blood flow in an upstream direction due to operation of the pressure mechanism.

For some applications, the pressure mechanism includes:
one or more electrodes; and
a control unit, couplable to the one or more electrodes.

For some applications, the electrodes are configured to be placed in contact with the artery.

For some applications, the control unit is configured to drive the electrodes to drive a contraction-inducing current into the artery during diastole.

For some applications, the control unit is configured to withhold driving the electrodes to drive a current into the artery during systole.

For some applications, the pressure mechanism includes a cuff, configured to be placed around the artery, a mechanical compressor, a pump, or a solenoid.

For some applications, the sensor is configured to generate the signal in response to detecting diastole. For some applications, the pressure mechanism is configured to respond to the generated signal by compressing the artery during diastole and releasing the compression during systole.

For some applications, the pressure mechanism is configured to increase a blood pressure in the artery by at least 30 mmHg, by compressing the artery.

For some applications, the valve is configured to be at least 1 cm upstream from the pressure mechanism.

For some applications, the pressure mechanism is configured to compress an artery that has an outer diameter between 0.5 and 2 mm, or between 2 and 10 mm.

For some applications, the valve is configured to be implanted in the artery, upstream of the site.

For some applications, the valve is configured to be implanted in an artery other than the artery to which the pressure mechanism is coupled.

For some applications, the valve is not physically coupled to the pressure mechanism.

There is further provided, in accordance with an application of the present invention, a method, including:

facilitating sensing of a cardiac cycle of a patient by coupling a sensor to the patient;

coupling a pressure mechanism, configured to respond to a signal from the sensor, to an artery of the patient; and implanting a valve at an arterial location of the patient, downstream of a native aortic valve site of the patient, the coupling of the pressure mechanism and the implanting of the valve being such that the implanted valve is upstream of the pressure mechanism.

For some applications, coupling the pressure mechanism to the artery of the patient includes implanting the pressure mechanism.

For some applications, coupling the pressure mechanism to the artery of the patient includes maintaining the pressure mechanism at an extracorporeal site, while it is coupled to the artery.

For some applications, facilitating the sensing includes coupling the sensor to a site of the artery of the patient.

For some applications, the pressure mechanism includes one or more electrodes, and coupling the pressure mechanism to the artery of the patient includes placing the one or more electrodes in contact with the artery.

For some applications, the pressure mechanism includes a cuff, and coupling the pressure mechanism to the artery of the patient includes placing the cuff around the artery.

For some applications, the pressure mechanism includes a mechanical compressor, and coupling the pressure mechanism to the artery of the patient includes placing the mechanical compressor around the artery.

For some applications, the pressure mechanism includes a pump, and coupling the pressure mechanism to the artery of the patient includes coupling the pump to the artery.

For some applications, the pressure mechanism includes a solenoid, and coupling the pressure mechanism to the artery of the patient includes coupling the solenoid to the artery.

For some applications, coupling the pressure mechanism to the artery includes coupling the pressure mechanism to an artery that has an outer diameter between 0.5 and 2 mm or between 2 and 10 mm.

For some applications, implanting the valve upstream of the pressure mechanism includes implanting the valve in the same artery to which the pressure mechanism is coupled.

For some applications, implanting the valve upstream of the pressure mechanism includes implanting the valve in an artery other than the artery to which the pressure mechanism is coupled.

For some applications, implanting the valve upstream of the pressure mechanism includes implanting a valve that is not physically coupled to the pressure mechanism.

There is further provided, in accordance with an application of the present invention, a method, including:

sensing a cardiac cycle of a patient;

enhancing blood flow in a downstream direction in an artery of the patient, by compressing the artery in response to the sensing of the cardiac cycle; and inhibiting blood flow in an upstream direction due to the compression of the artery.

For some applications, inhibiting the blood flow includes performing the inhibiting at an aortic site between a renal artery and an aortic bifurcation of the patient.

For some applications, inhibiting the blood flow in the upstream direction includes inhibiting the blood flow in the upstream direction using a valve. For some applications, inhibiting the blood flow in the upstream direction using the valve includes inhibiting blood flow in the upstream direction using a valve that is at least 1 cm upstream from a site of the compression of the artery. For some applications, inhibiting the blood flow in the upstream direction using the valve includes inhibiting the blood flow in the upstream direction using a valve that is physically separated from a site of the compression of the artery.

For some applications, sensing includes sensing diastole of the patient, and wherein compressing the artery includes compressing the artery in response to the sensing of diastole. For some applications, sensing further includes sensing systole of the patient, and compressing the artery includes withholding compressing the artery in response to the sensing of systole.

For some applications, sensing includes sensing diastole of the patient, and compressing the artery includes driving a contraction-inducing current in to the artery in response to the sensing of diastole. For some applications, sensing further includes sensing systole of the patient, and compressing the artery includes withholding driving a contraction-inducing current to the artery in response to the sensing of systole.

For some applications, compressing the artery includes compressing an artery that has an outer diameter between 0.5 and 2 mm or between 2 and 10 mm.

There is further provided, in accordance with an application of the present invention, a method, including:

identifying a patient as suffering from a vascular disease; and in response to identifying as suffering from a vascular disease, implanting a valve in an aorta of the patient, at least 5 cm downstream of a native aortic valve site of the patient.

For some applications, implanting the valve includes implanting the valve at an aortic site located between a renal artery and an aortic bifurcation of the patient. For some applications, implanting the valve in the aorta includes implanting the valve within 5 cm of an aortic bifurcation.

For some applications, the method includes implanting an artificial blood vessel downstream of an implantation site of the valve. For some applications, implanting the artificial blood vessel includes implanting two artificial blood vessels, at contralateral sites of the patient.

For some applications, implanting the artificial blood vessel includes implanting an artificial blood vessel that is configured to increase its cross-sectional area by at least 20 percent during systole.

For some applications, implanting the artificial blood vessel includes implanting an artificial blood vessel that is configured to change its cross-sectional shape from elliptical to circular, during systole.

The present invention will be more fully understood from the following detailed description of applications thereof, taken together with the drawings, in which:

DETAILED DESCRIPTION OF APPLICATIONS

Figure 1A:
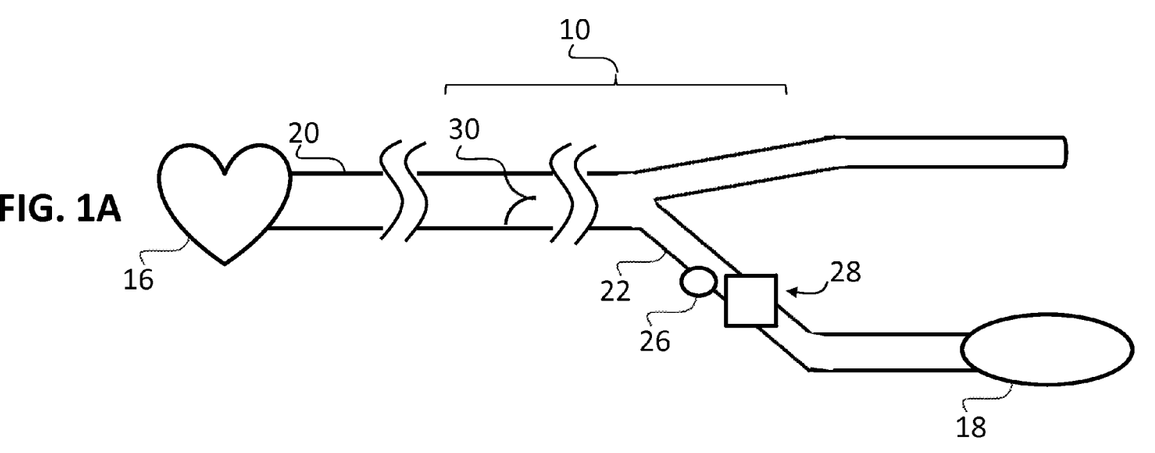
FIGS. 1A-B are schematic illustrations of respective configurations of a system for enhancing blood flow in a blood vessel, in accordance with some applications of the present invention.

Reference is made to FIG. 1A, which is a schematic illustration of medical apparatus 10, comprising a sensor 26, a pressure mechanism 28 and a valve 30. A heart 16 of a patient supplies blood to an artery 20 that is coupled to, and supplies, an artery 22. Artery 22 may be a native artery, or it may comprise an arterial graft (either made of natural materials or artificial materials). In accordance with some applications of the present invention, sensor 26, in response to detecting diastole, sends a signal to pressure mechanism 28, which is coupled to artery 22 of the patient. Pressure mechanism 28 is configured to respond to the generated signal from sensor 26 by compressing the artery during diastole, thereby enhancing blood flow to a downstream organ 18, and releasing the compression during systole. Compression of artery 22 typically generates a blood pressure of at least 140 mmHg, e.g., above 170 mmHg, but below 250 mmHg. The increase in blood pressure in the artery due to the compression, relative to the diastolic pressure within artery 22 in the absence of compression being applied, is typically at least 30 mmHg, e.g. at least 40 mmHg and/or less than 90 mmHg.

According to one application of the present invention, artery 22 has an outer diameter between 0.5 and 2 mm. According to another application of the present invention, artery 22 has an outer diameter between 2 and 10 mm.

According to some applications of the present invention, valve 30 is implanted in an artery 20, upstream of artery 22 to which pressure mechanism 28 is coupled, thereby inhibiting blood flow in an upstream direction due to the operation of pressure mechanism 28. For example, the valve may be implanted in the aorta and the pressure mechanism may be coupled to the renal artery, the iliac artery, and/or the femoral artery. According to some applications of the present invention, valve 30 is not physically coupled to pressure mechanism 28, and is, for example, at least 1 cm upstream from pressure mechanism 28 (e.g., more than 10 cm, less than 50 cm, and/or 10-50 cm upstream from pressure mechanism 28).

Figure 1B:
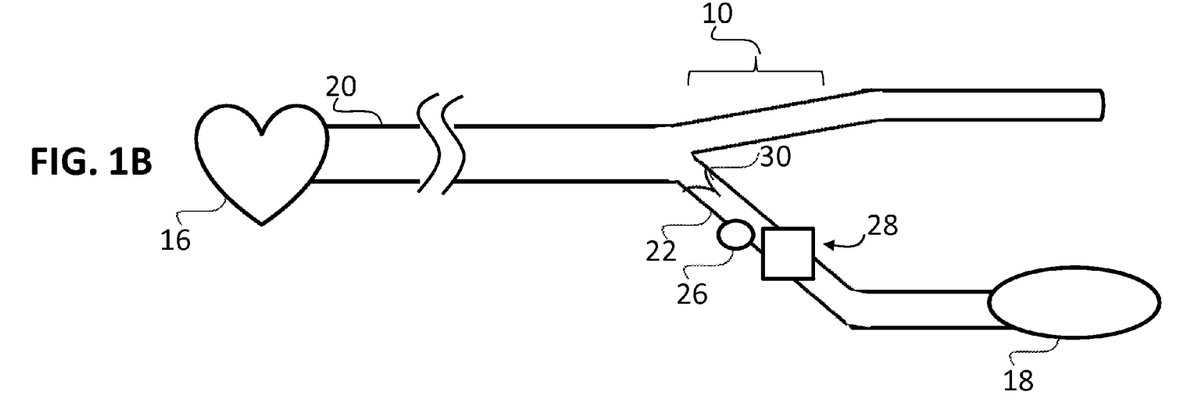

Reference is now made to FIG. 1B, which is a schematic illustration of medical apparatus 10, comprising generally the same components as shown in FIG. 1A, except that valve 30 is implanted upstream of pressure mechanism 28 in artery 22 to which pressure mechanism 28 is coupled, thereby inhibiting blood flow in an upstream direction due to the operation of pressure mechanism 28. For example, both the valve and the pressure mechanism may be coupled to the aorta, the renal artery, the iliac artery, and/or the femoral artery.

Figure 2:
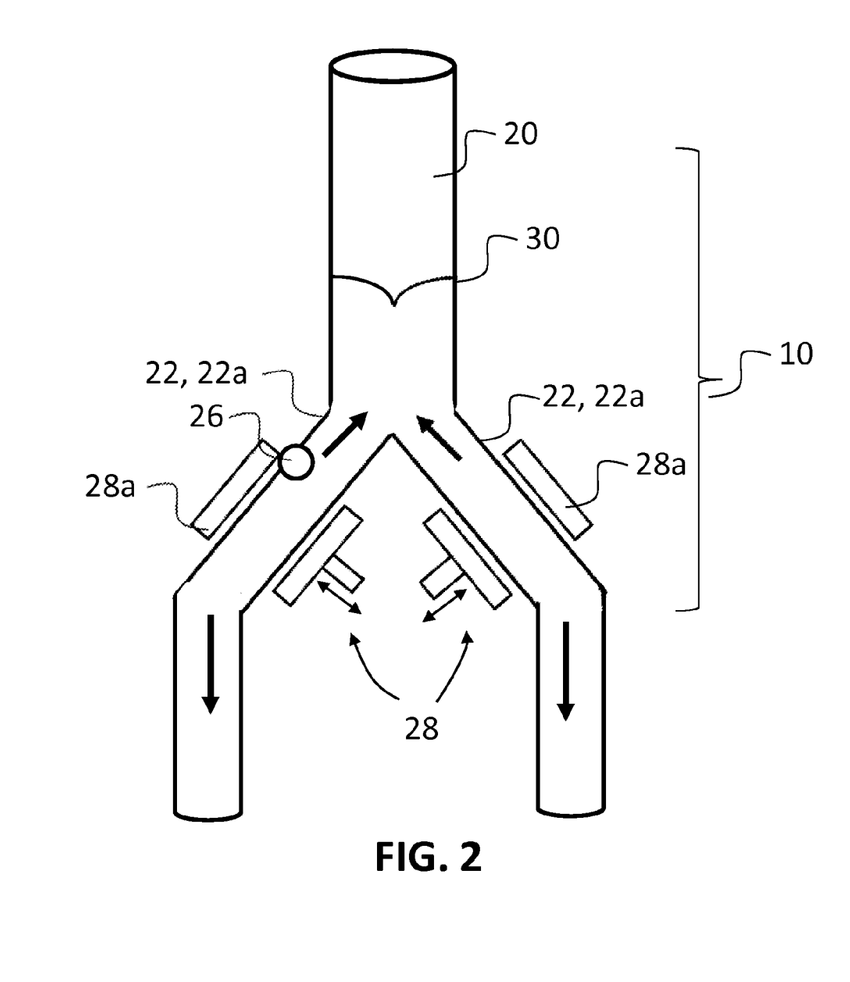
FIG. 2 is a schematic illustration of a system for enhancing blood flow in a blood vessel, in accordance with some applications of the present invention.

Reference is now made to FIG. 2, which is a schematic illustration of medical apparatus 10, comprising generally the same components as shown in FIG. 1. According to one application of the present invention, artery 22, as seen in FIG. 1, comprises an iliac or a femoral artery 22a. According to one application of the present invention, pressure mechanism 28, as seen in FIG. 1, comprises a mechanical compressor 28a. Pressure mechanism 28a may also comprise a cuff, a pump or a solenoid, configured to cyclically press a compressing element against artery 22.

Figure 3:
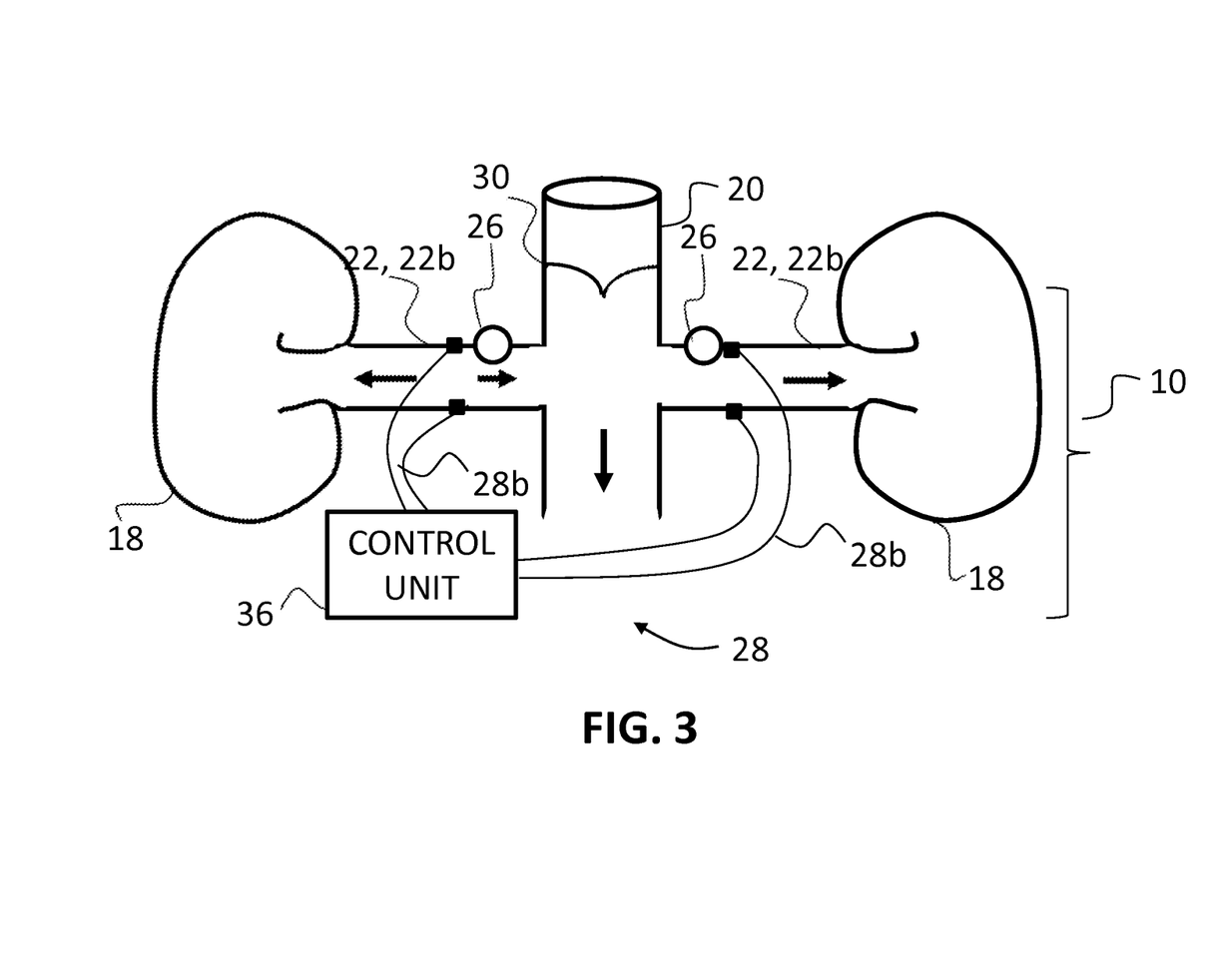
FIG. 3 is a schematic illustration of another system for enhancing blood flow in a blood vessel, in accordance with some applications of the present invention.

Reference is now made to FIG. 3, which is a schematic illustration of medical apparatus 10, comprising generally the same components as shown in FIG. 1. According to one application of the present invention, artery 22, as seen in FIG. 1, comprises a renal artery 22b. According to one application of the present invention, pressure mechanism 28, as seen in FIG. 1, comprises one or more electrodes 28b coupled to a control unit 36. According to one application of the present invention, sensor 26 sends a signal to control unit 36, which is configured to drive electrodes 28b to drive a contraction-inducing current to artery 22, in response to the sensor signal. The control unit sets parameters of the current to be such as to induce contraction of muscle of the artery, and to thereby enhance blood flow in the artery leading to a kidney 18. For example, suitable parameters include inducing contraction during diastole.

Figure 4:
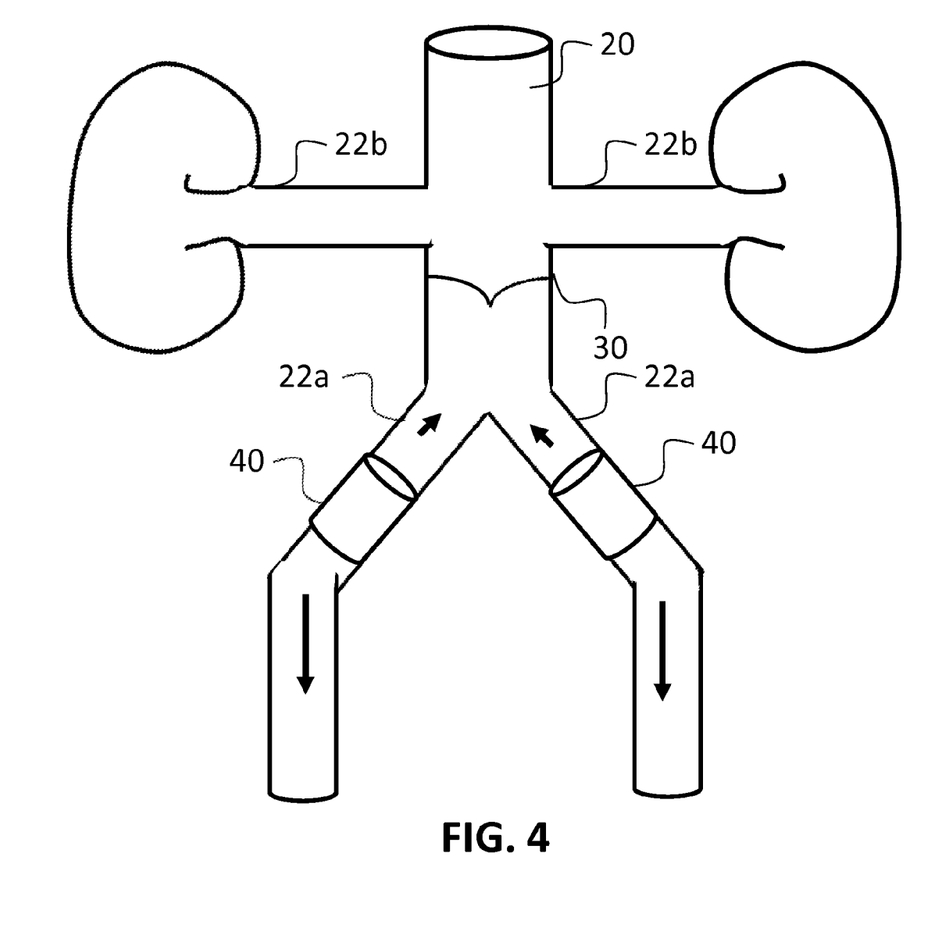
FIG. 4 is a schematic illustration of another system for enhancing blood flow in a blood vessel, in accordance with some applications of the present invention.

Reference is now made to FIG. 4, which is a schematic illustration of valve 30, configured to be implanted in an aorta of the patient. For example, as shown in FIG. 4, valve 30 may be implanted at a site located between a renal artery 22b and an aortic bifurcation of the patient (where the aorta bifurcates into the two iliac arteries 22a), e.g., within 5 cm of the bifurcation. According to one application of the present invention, a graft 40 is implanted in communication with iliac artery 22a or in communication with the femoral artery, replacing a damaged portion of iliac artery 22a. Typically, graft 40 is implanted downstream of valve 30. For some applications, two grafts 40 are implanted (as shown in FIG. 4), at contralateral sites.

It is noted that the application of the invention shown in FIG. 4 typically operates without any active, powered elements. As described hereinabove, for some applications of the present invention, graft 40 is compliant, and changes its cross-sectional area according to the cardiac cycle of the patient. For example, the graft expands during systole, and contracts during diastole. Typically, the diastolic contraction of the graft squeezes out blood that is in the contracting area of the graft. According to one application of the present invention, the implanted valve inhibits the upstream flow of blood from the contracting graft, therefore enhancing the blood flow in a downstream direction due to the contraction of the graft. Although typically the valve is implanted in the aorta, for some applications, the valve may be implanted in an artery which is smaller in diameter than the aorta.

According to one application of the present invention, the graft expands during systole without any change in the shape of the graft (e.g., both the pre-expansion and post-expansion shapes of the graft may be circular). Alternatively, the graft changes its cross-sectional shape from an ellipse in diastole to a circle in systole. The cross-sectional area thus goes up substantially during systole.

For some applications of the present invention, the valve is physically coupled to the graft.

It is noted that, although certain combinations of implantation locations, grafts and pressure mechanisms are described with reference to FIGS. 1-4, the scope of the present invention includes combining the implantation locations, grafts, and pressure mechanisms with each other, as would be obvious to one skilled in the art upon reading the above description. For example, the scope of the present invention includes placing an electrode-based pressure mechanism (as described with reference to FIG. 3), in the femoral artery (FIG. 2), or the aorta, or placing a mechanical pressure mechanism (FIG. 2) in the renal artery (FIG. 3), or in the aorta. In addition, the scope of the present invention includes coupling a graft to an artery other than the iliac artery or the femoral artery and placing a valve at an upstream location therefrom, in accordance with the techniques described hereinabove.

The implantation of apparatus shown in FIGS. 1-4 may be performed in open surgery, or minimally invasively.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   facilitating sensing of a cardiac cycle of a patient by coupling a sensor to the patient;
   coupling a pressure mechanism, configured to respond to a signal from the sensor, to an artery of the patient; and
   implanting a valve at an arterial location of the patient, downstream of a native aortic valve site of the patient, the coupling of the pressure mechanism and the implanting of the valve being such that the implanted valve is upstream of the pressure mechanism.

2. The method according to claim 1, wherein the pressure mechanism includes one or more electrodes, and wherein coupling the pressure mechanism to the artery of the patient comprises placing the one or more electrodes in contact with the artery.

3. The method according to claim 1, wherein the pressure mechanism includes a mechanical compressor, and wherein coupling the pressure mechanism to the artery of the patient comprises placing the mechanical compressor around the artery.

4. The method according to claim 1, wherein implanting the valve upstream of the pressure mechanism comprises implanting the valve in the same artery to which the pressure mechanism is coupled.

5. The method according to claim 1, wherein implanting the valve upstream of the pressure mechanism comprises implanting the valve in an artery other than the artery to which the pressure mechanism is coupled.

6. The method according to claim 1, wherein implanting the valve upstream of the pressure mechanism comprises implanting a valve that is not physically coupled to the pressure mechanism.

* * * * *